US00PP16665P2

(12) United States Plant Patent
Talmadge

(10) Patent No.: US PP16,665 P2
(45) Date of Patent: Jun. 20, 2006

(54) ***DIASCIA* PLANT NAMED 'BALWHISAPTIM'**

(50) Latin Name: *Diascia barbaraeXDiascia integerimmaXDiascia mollis*
Varietal Denomination: Balwhisaptim

(75) Inventor: Paul A. Talmadge, Guadalupe, CA (US)

(73) Assignee: Ball Horticultural Company, West Chicago, IL (US)

( * ) Notice: Subject to any disclaimer, the term of this patent is extended or adjusted under 35 U.S.C. 154(b) by 103 days.

(21) Appl. No.: 11/015,394

(22) Filed: Dec. 17, 2004

(51) Int. Cl.
*A01H 5/00* (2006.01)

(52) U.S. Cl. ..... Plt./263

(58) Field of Classification Search ..... Plt./263
See application file for complete search history.

*Primary Examiner*—Anne Marie Grunberg
(74) *Attorney, Agent, or Firm*—Wood, Phillips, Katz, Clark & Mortimer

(57) ABSTRACT

A new and distinct *Diascia* plant named 'Balwhisaptim' characterized by its apricot-colored flowers, medium green-colored foliage, and vigorous, mounded, and spreading growth habit.

1 Drawing Sheet

Latin name of genus and species of plant claimed: *Diascia barbaraeXDiascia integerimmaXDiascia mollis.*
Variety denomination: 'Balwhisaptim'.

BACKGROUND OF THE INVENTION

The present invention relates to a new and distinct cultivar of Interspecific *Diascia* plant hereinafter referred to by the cultivar name 'Balwhisaptim'.

The new cultivar originated in a controlled breeding program during the autumn of 2000, at Guadalupe, Calif. The objective of the breeding program was the development of *Diascia* cultivars with a well-branched, spreading growth habit, continuous flowering, and medium green-colored foliage.

The female (seed) parent of the new cultivar was the proprietary Interspecific *Diascia* breeding selection designated 1624-1, not patented, characterized by its large pink-colored flowers and bush type habit. The male (pollen) parent of the new cultivar was the proprietary Interspecific *Diascia* breeding selection designated 1646-1, not patented, characterized by its coral-colored flowers and prostrate habit. The new cultivar was discovered and selected by the inventor as a single flowering plant within the progeny of the above stated cross in autumn 2002.

Asexual reproduction of the new cultivar by terminal stem cuttings since autumn 2002 at Guadalupe, Calif. and West Chicago, Ill. has demonstrated that the new cultivar reproduces true to type with all the characteristics, as herein described, firmly fixed and retained through successive generations of such asexual propagation.

SUMMARY OF THE INVENTION

The new cultivar has not been observed under all possible environmental conditions to date. Accordingly, it is possible that the phenotype may vary somewhat with variations in the environment, such as temperature, light intensity, and day length without, however, any variance in genotype.

The following characteristics of the new cultivar have been repeatedly observed and can be used to distinguish 'Balwhisaptim' as a new and distinct cultivar of *Diascia* plant:

1. Apricot-colored flowers.
2. Medium green-colored foliage.
3. Vigorous, mounded, and spreading growth habit.

Plants of the new cultivar differ from plants of the female parent primarily in flower color and growth habit, and from plants of the male parent primarily in flower color and growth habit.

Of the many *Diascia* cultivars know to the inventor, the most similar to the new cultivar is the cultivar Diastina, U.S. Plant Pat. No. 13,932. However, in side-by-side comparisons, plants of the new cultivar differed from plants of 'Diastina' in the following characteristics:

1. Plants of the new cultivar have darker foliage than Plants of 'Diastina'.
2. Plants of the new cultivar have different flower color than plants of 'Diastina'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the values cited in the detailed description, which accurately describes the colors of 'Balwhisaptim'. The plants were grown in 10 cm pots for 11 weeks in a greenhouse at West Chicago, Ill.

DETAILED BOTANICAL DESCRIPTION

Figure 1:
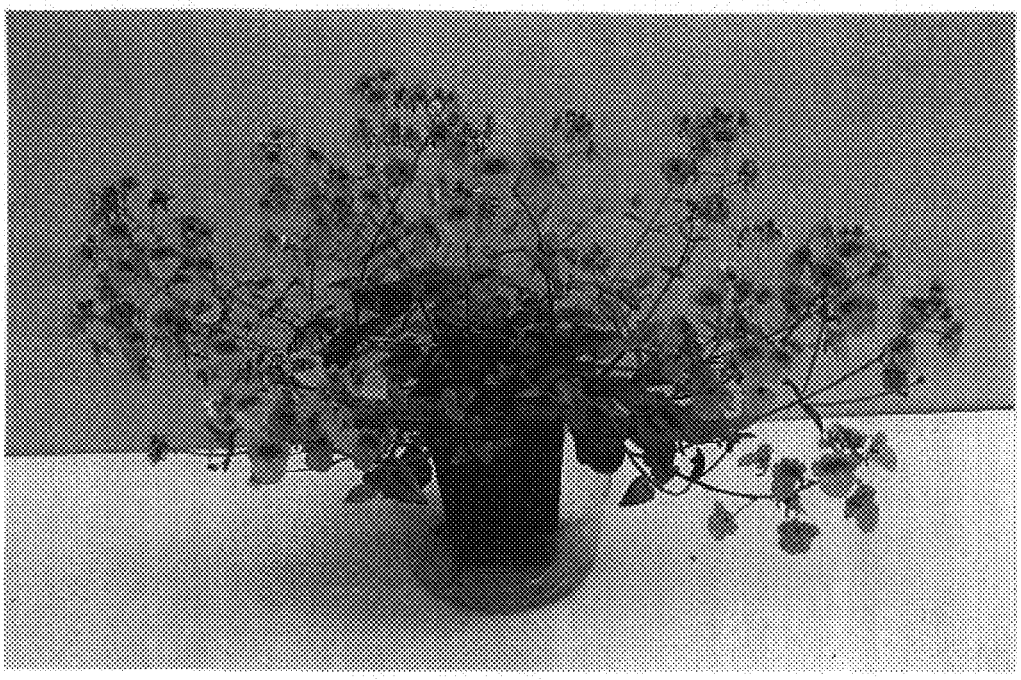
FIG. 1 illustrates a side view of the overall growth and flowering habit of 'Balwhisaptim'.
Figure 2:
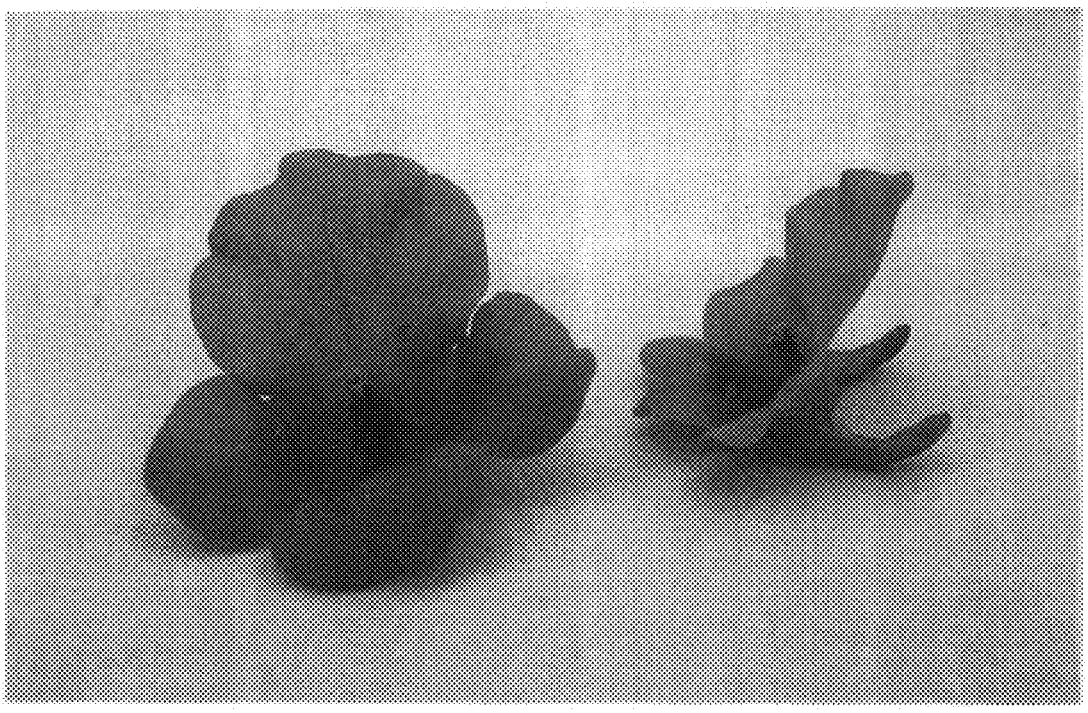
FIG. 2 illustrates a close-up side view and front view of individual flowers of 'Balwhisaptim'.

The chart used in the identification of colors described herein is The R.H.S. Colour Chart of The Royal Horticultural Society, London, England, 2001 edition, except where general color terms of ordinary significance are used. The color values were determined on Nov. 8, 2004 between 8:00 and 9:00 a.m. under natural light conditions.

The following descriptions and measurements describe plants produced from terminal stem cuttings from stock plants and grown in a double polycarbonate-covered greenhouse under conditions comparable to those used in commercial practice. The plants were grown at West Chicago, Ill. in 10 cm pots for 11 weeks while utilizing a soilless growth medium. Greenhouse temperatures were maintained at approximately 62°–75° F. (17°–24° C.) during the day and approximately 52°–60° F. (11°–15° C.) during the night. Greenhouse light levels were maintained at 5,000 to 8,000 footcandles during the day.

Botanical classification: Interspecific *Diascia* cultivar Balwhisaptim.

Parentage:

*Female parent.*—Proprietary Interspecific *Diascia* breeding selection designated 1624-1, not patented.

*Male parent.*—Proprietary Interspecific *Diascia* breeding selection designated 1646-1, not patented.

Propagation:

*Type cutting.*—Terminal stem cutting.

*Time to initiate roots.*—Approximately 6 to 9 days.

*Time to produce a rooted cutting.*—Approximately 3 to 4 weeks.

*Root description.*—Fine, fibrous.

*Rooting habit.*—Freely branching.

Plant description:

*Crop time.*—Approximately 5 to 7 weeks from planting of a rooted cutting in a 10 cm pot.

*Habit of growth.*—Vigorous. Freely branching with branches forming at every node.

*Form.*—Spreading mounded.

*Size.*—Height: Approximately 19.6 cm. Diameter (area of spread): Approximately 48.4 cm.

*Branch description.*—Quantity: Approximately 39 flowering branches. Strength: Moderate. Shape: Square in cross section. Length: Approximately 25.6 cm. Diameter: Approximately 2 mm. Internode length at middle of branch: Approximately 3.2 cm. Texture: Glabrous. Color: 144A.

*Foliage.*—Quantity of leaves per branch: Approximately 9. Fragrance: None. Type: Simple. Arrangement: Opposite. Leaf orientation to stem: Obtuse. Shape: Ovate. Apex: Cuspidate. Base: Cordate. Margin: Entire. Venation pattern: Pinnate. Length: Approximately 2.1 cm. Width: Approximately 1.5 cm. Texture of upper and lower surfaces: Glabrous. Color of mature foliage: Upper surface: 137A with venation of 145A. Lower surface: Between 138A and 138B with venation of 145A. Petiole length: Approximately 3.5 mm. Petiole diameter: Approximately 1 mm. Petiole texture: Upper and lower surfaces: Glabrous. Petiole color: 143A.

Flowering description:

*Time to first flower.*—Approximately 5–7 weeks after planting of rooted cutting.

*Flowering habit.*—Freely flowering under outdoor growing conditions with substantially continuous blooming from spring through autumn and year round in greenhouse environment.

Inflorescence description:

*Type.*—Terminal clusters.

*Size.*—Length (depth): Approximately 4.6 cm. Width: Approximately 5 cm.

Flower description:

*Lastingness of a single bloom.*—Approximately 4–5 days.

*Quantity per inflorescence.*—Approximately 6.

*Type.*—Solitary, not persistent, five lobed, zygomorphic, with two nectar spurs.

*Fragrance.*—None detected.

*Aspect.*—Concave.

*Shape.*—Obovate.

*Flower size.*—Width: Approximately 2.2 cm. Length: Approximately 2.3 cm. Depth, including spurs: Approximately 9 mm.

*Petals.*—Quantity: Five, two upper petals, two lateral petals and one lower petal. Type: Imbricate, fused at base. Aspect: Cupped. Apex: Obtuse. Margin: Entire. Appearance: Iridescent. Color: Upper surface: Closest to 37B. Color of lower surface: Closest to 37C. Indentation at base of upper petals: Length: 3 mm. Width: 3.5 mm. Color: 3A.

*Two upper (banner) petals.*—Length: Approximately 5 mm. Width: Approximately 4 mm. Texture of upper surface: Glabrous. Texture of lower surface: Glabrous except for sparse stipulate glands at base.

*Lateral petals.*—Length: Approximately 8 mm. Width: Approximately 6 mm. Texture of upper surface: Glabrous. Texture of lower surface: Glabrous except for sparse stipulate glands at base. Sharply curved nectar spurs form at base of each of the lateral petals.

*Nectar spurs.*—Length: 6 mm. Diameter at petal attachment: 3 mm. Diameter at tip: 1 mm. Texture: Sparsely stipulate glandular. Color: 51C with tip of 58A.

*Lower petal.*—Length: Approximately 9 mm. Width: Approximately 1.3 cm. Texture of upper surface: Glabrous. Texture of lower surface: Glabrous except for sparse stipulate glands at base. Gland color: N186A.

*Calyx.*—Shape: Five pointed star, formed by 5 sepals fused at base. Length: Approximately 3 mm. Diameter: Approximately 6 mm. Sepal shape: Lanceolate. Sepal apex: Acute. Sepal margin: Entire. Sepal length: Approximately 2.8 mm. Sepal width: Approximately 1 mm. Texture of upper/inner surface of sepals: Glabrous. Texture of outer/lower surface of sepals: Stipulate glandular. Gland color: N186A. Color of upper and lower sepal surfaces is 143C.

*Peduncle.*—Strength: Moderate. Aspect: At acute angle to stem. Length: Approximately 1.7 cm. Diameter: Approximately 0.4 mm. Texture: Stipulate glandular. Gland color: 186A. Color: 143A.

*Bud (at first color).*—Shape: Globular. Length: Approximately 4.2 mm in length. Diameter: Approximately 6 mm. Texture: Glabrous. Color: 37D.

*Reproductive organs.*—Androecium: There are 4 stamens per flower. Filament length: 3 mm. Filament color: 59B. Anther shape: Oval. Anther length: 1 mm. Anther color: 9C. Pollen amount: Moderate. Pollen color: 12A. Gynoecium: Pistil number: One per flower. Pistil length: 3.3 mm. Stigma shape: Round. Stigma length: 0.5 mm. Stigma color: 155D. Style length: Approximately 2 mm. Style color: 145C. Ovary length: Approximately 0.7 mm. Ovary color: 143A.

Seed and fruit production: Neither seed nor fruit production has been observed.

Disease and pest resistance: Resistance to pathogens or pests common to *Diascia* has not been observed.

What is claimed is:

1. A new and distinct cultivar of Interspecific *Diascia* plant named 'Balwhisaptim', substantially as herein shown and described.

* * * * *